United States Patent [19]

DiCola et al.

[11] 3,964,868
[45] June 22, 1976

[54] ORGANIC CARBON ANALYZER SYSTEM

[75] Inventors: Louis S. DiCola, Lincoln, R.I.; Donald W. Kemp, Marion, Mass.; H. Duane Evans, Portsmouth, R.I.

[73] Assignee: Raytheon Company, Lexington, Mass.

[22] Filed: May 24, 1974

[21] Appl. No.: 473,116

[52] U.S. Cl. .................. 23/253 PC; 23/230 PC; 210/180; 261/126
[51] Int. Cl.² ................................ G01N 31/12
[58] Field of Search ............... 23/230 PC, 253 PC; 55/199, 200, 201, 204, 205; 210/180; 261/126, DIG. 70

[56] References Cited
UNITED STATES PATENTS

| | | | |
|---|---|---|---|
| 3,296,435 | 1/1967 | Teal et al. | 23/230 PC X |
| 3,322,504 | 5/1967 | Capuano | 23/230 PC |
| 3,607,071 | 9/1971 | Staffin | 23/230 PC |
| 3,854,881 | 12/1974 | Cohen | 23/253 PC |

OTHER PUBLICATIONS

Alves, *Chem. Engr. Prog.*, vol. 66(7); pp. 60–67 (1970).

Anderson et al., *Chem. Engr.*, vol. 73, pp. 139–144 (12-6-1965).

*Primary Examiner*—Morris O. Wolk
*Assistant Examiner*—Timothy W. Hagan
*Attorney, Agent, or Firm*—David M. Warren; Joseph D. Pannone; Milton D. Bartlett

[57] ABSTRACT

An organic carbon analyzer system particularly adapted for the continuous analysis of raw sewage of a municipality. A gaseous transport is provided for carrying acidified liquid sewage including dispersed particulate matter through an elongated aeration chamber wherein carbon dioxide evolved from inorganic salts diffuses away from the sewage and into the gas. A second gaseous transport free of carbon dioxide and including an oxidizing agent then carries the sewage into a heated chamber having a tortuous interior surface which provides sufficient retention time to oxidize organic carbonaceous materials of the sewage resulting in a second evolution of carbon dioxide. An analyzer provides a continuous reading of the concentration of the carbon dioxide produced in the heated chamber.

18 Claims, 10 Drawing Figures

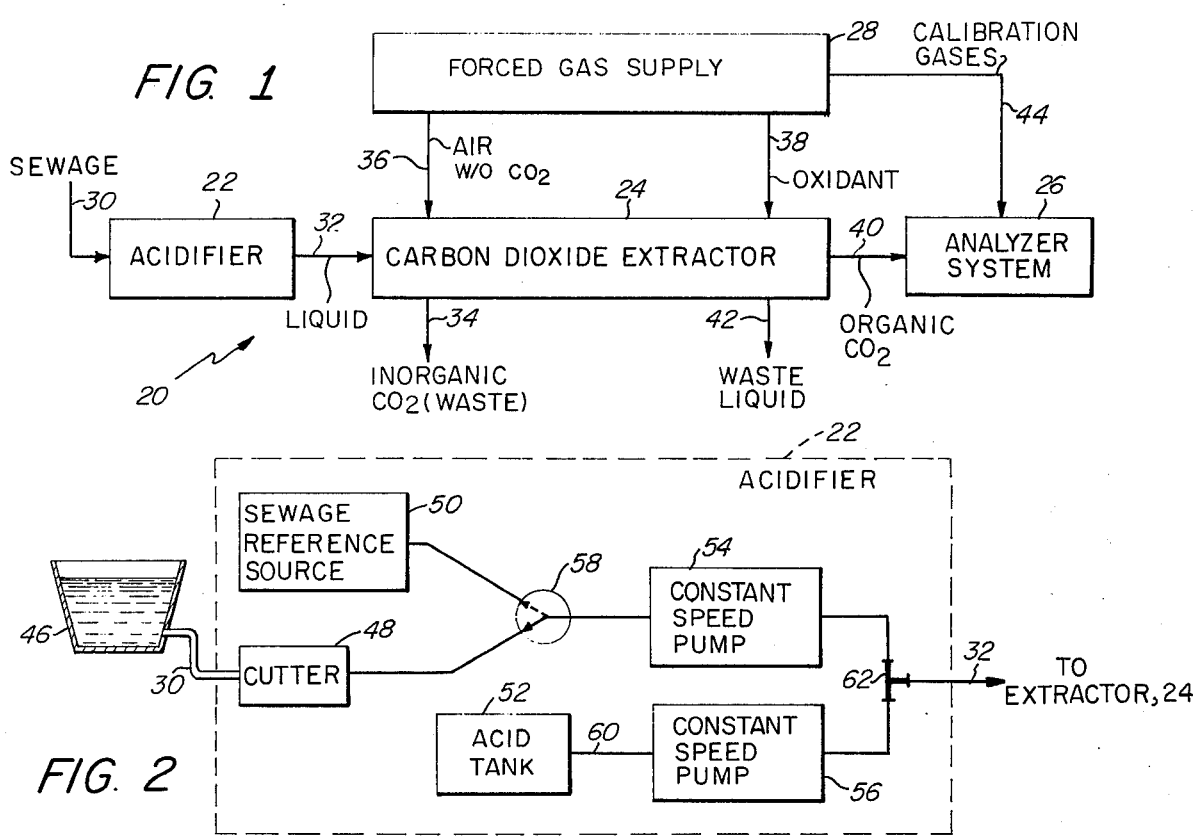
FIG. 1
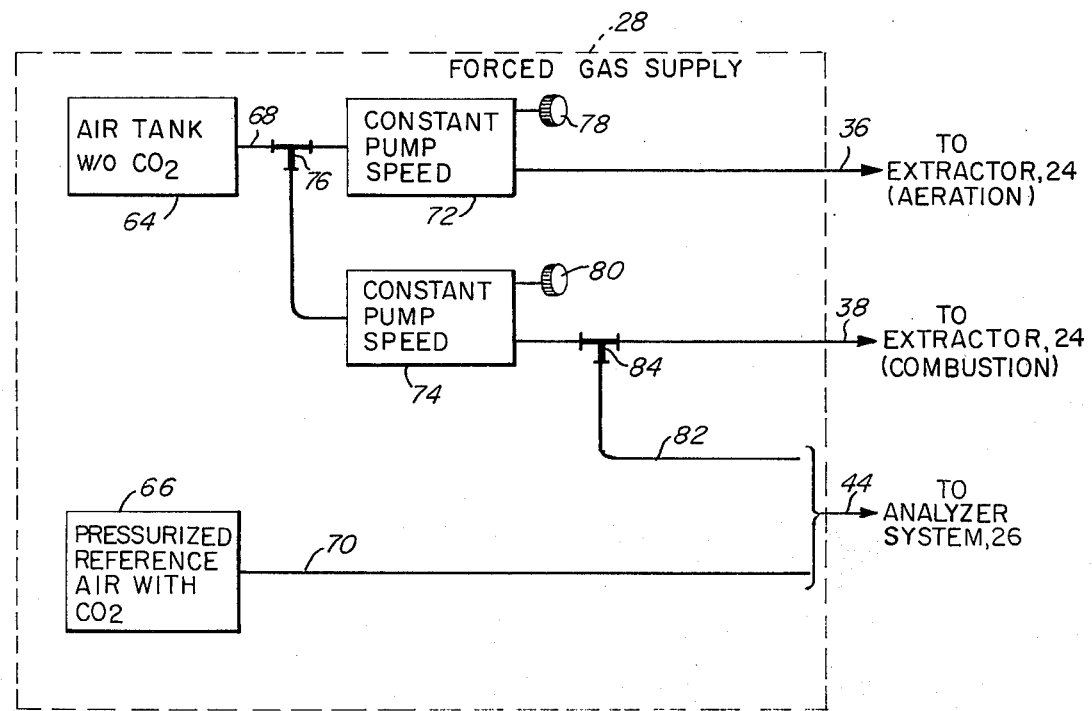
FIG. 2
FIG. 3

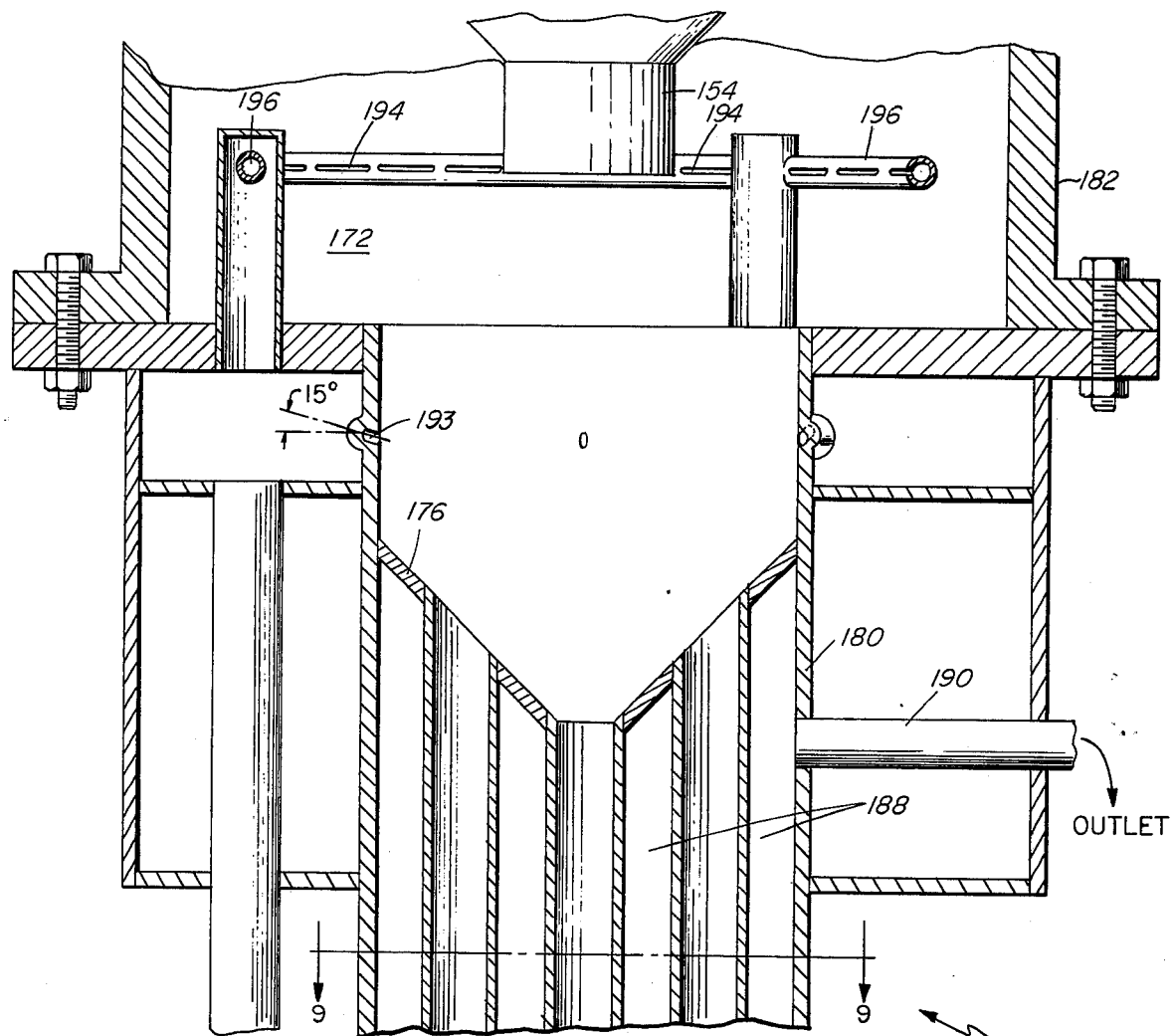
FIG. 8
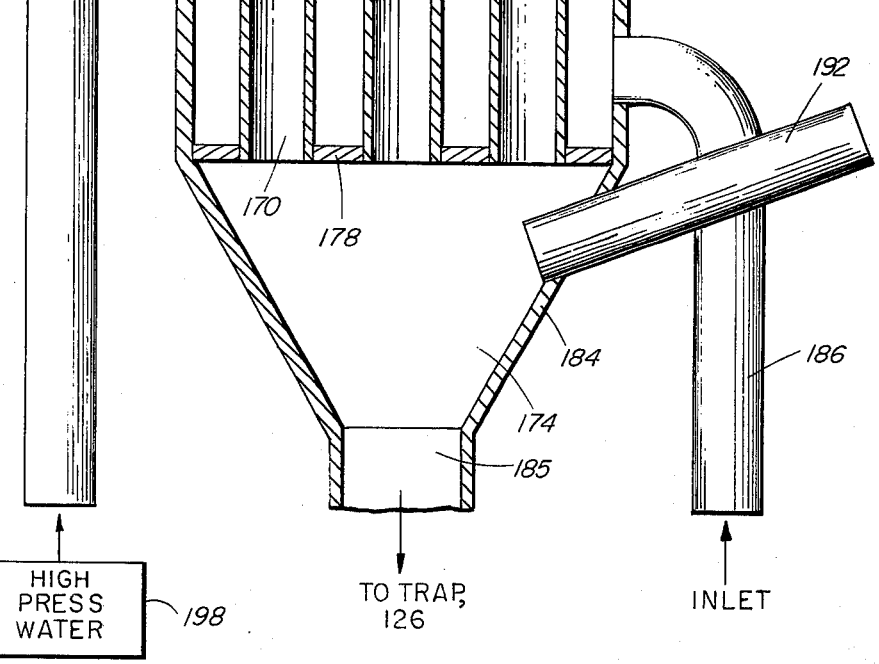

3,964,868

ORGANIC CARBON ANALYZER SYSTEM

BACKGROUND OF THE INVENTION

This invention relates to a system providing a continuous monitoring of organic carbonaceous matter and, more particularly, a system adapted to continuously monitor raw sewage by the separation of organic and inorganic sources of carbonaceous matter and the measurement of carbon dioxide by the use of a gaseous transport which renders the equipment substantially free of clogging by the sewage.

There is growing interest in the protection of the environment from the by products of industry such as the discharge of sewage into a river. Such industrial waste frequently contains polluting matter which must be carefully monitored for proper control of pollutants in a program of environmental protection. One class of pollutants is of organic matter, the concentration of which may be measured by chemical reactions in which the carbon of the organic matter is combined with oxygen in which case the amount of carbon dioxide produced or the amount of oxygen consumed is utilized as a measure of the carbon and, hence, of the concentration of the organic matter. Examples of such processes are shown in U.S. Pat. No. 3,322,504 which issued in the name of I. A. Capuano on May 30, 1967; U.S. Pat. No. 3,459,938 which issued in the name of V. A. Stenger et al. on Aug. 5, 1969; and U.S. Pat. No. 3,703,355 which issued in the name of Y. Takahashi et al. on Nov. 21, 1972.

The prior art teaches a number of systems for the measurement of carbon and oxygen by the generation of carbon dioxide, the amount thereof being measured with an infrared spectrometer. Some of these prior art systems include combustion chambers adapted for the combusting of measured discrete samples of sewage or other matter which is to be analyzed. Inorganic material is removed in some of these systems by a precipitation procedure.

A problem arises in that precise monitoring of the substances in raw sewage necessitates the use of equipment capable of providing a continuous measurement of the amount of inorganic carbonaceous matter present in the raw sewage. A further problem arises in that the materials of the raw sewage tend to precipitate along the interior surfaces of tubes and chambers of the equipment thereby clogging the equipment and rendering it useless. Such clogging frequently necessitates a staff of support personnel who shutdown the equipment at regular intervals for unclogging the equipment while, in many municipal installations, it would be preferable to operate the installation with little or no staff.

SUMMARY OF THE INVENTION

The aforementioned problems are overcome and other advantages are provided by a system comprising, in accordance with the invention, two chambers for containing chemical reactions and two streams of gas which serve as transports for carrying sewage matter, respectively, through the two chambers. Thus, there are provided an elongated chamber and a gaseous transport for carrying acidified sewage therethrough, the elongated chamber providing a sufficiently long dwell time during which acid, previously added to the sewage, can react with inorganic salts to evolve carbon dioxide which diffuses into the gas of the transport to effect the separation of carbon dioxide of inorganic sources from the sewage. The gas and the liquid sewage experience a turbulent fluid flow in the chamber which ensures a thorough mixing of the acid with the sewage and the mixing of the sewage with the gas to ensure a thorough removal of the evolved carbon dioxide. The gas is then separated from the liquid by means of a gravity-operated trap in the form of a tee which permits the liquid portion of the fluid to settle in a downwardly projecting leg of the tee.

The liquid sewage is then metered into a rapidly moving stream of gas containing an oxidizing agent, such as oxygen, which produces a turbulent flow of the gas with droplets of the liquid, this gas serving as a transport for carrying the liquid into a heated combustion chamber having, in a preferred embodiment, a tortuous interior surface provided by means of alumina balls positioned between inconel walls, which ensures a sufficiently long retention time within the combustion chamber to provide thorough oxidation of organic carbonaceous matter of the sewage, this oxidation resulting in a second evolution of carbon dioxide. The effluent of the combustion chamber is then chilled in a condensing unit to separate the water of the sewage from the carbon dioxide and unused oxygen of the gaseous transport. The carbon dioxide concentration is then measured by an infrared spectrometer. The use of the turbulent flowing gaseous transport in the elongated aeration chamber significantly inhibits the formation of a precipitate on the interior walls of the chamber thereby eliminating a source of clogging. A flushing system is provided for forcing cold water through the combustion chamber at intervals of approximately one week, each flushing operation lasting approximately one to three hours during which times the thermally induced dimensional changes resulting from the sudden cooling from a typical operating temperature of 850°C loosen any precipitate or scale which may have formed to facilitate the dissolving of such scale in the flushing water. For example, such scale may include salts, such as sodium chloride, which is deposited when the water of the sewage is converted to steam. A major portion of the time elapsed during the one-to-three hour flushing operation is utilized for reheating the combustion chamber to bring it back up to operating temperature.

BRIEF DESCRIPTION OF THE DRAWINGS

The aforementioned features and other aspects of the invention are explained in the following description taken in connection with the accompanying drawings wherein:

FIG. 1 is a block diagram of an organic carbon analyzer system in accordance with the invention;

FIG. 2 is a block diagram of an acidifier of FIG. 1 utilized in acidifying raw sewage;

FIG. 3 is a block diagram of a forced gas supply of FIG. 1 which provides the gaseous transports as well as reference gases for calibrating a carbon dioxide analyzer utilized in the system of FIG. 1;

FIG. 8 is an axial sectional view of a condenser utilized in an alternative embodiment of the invention for cooling the effluent of the combustion chamber taken along the lines 8—8 of FIG. 9;

DETAILED DESCRIPTION

Figure 4:
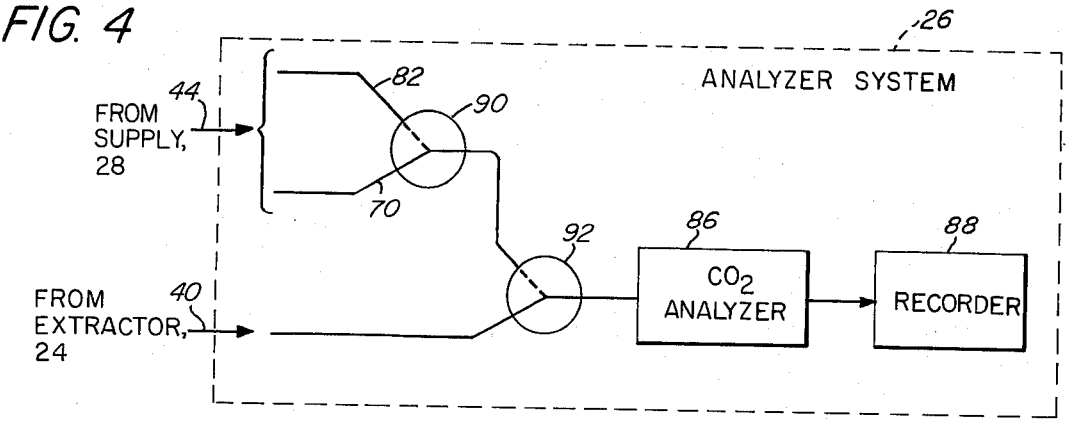
FIG. 4 is a diagram of an analyzer system of FIG. 1.

Referring now to FIG. 1, there is seen a system 20 for extracting carbon dioxide from the materials contained within raw sewage in accordance with the invention, and for measuring the concentration of the portion of carbon dioxide evolved from organic carbonaceous matter. The system 20 is seen to comprise an acidifier 22, an extractor 24 of carbon dioxide, a system 26 for measuring the concentration of the carbon dioxide, and a supply 28 of gases which are applied to the extractor 24 to serve as fluid transports and to the analyzer system 26 for calibrating an analyzer of carbon dioxide contained therein. Raw sewage is applied continuously along line 30 to the acidifier 22 which, preferably includes means (not shown), such as that disclosed in copending application Ser. No. 440,439 filed in the names of G. E. Anderson and G. V. Morris, that cuts and grinds solid matter of the sewage into particulate matter which is sufficiently fine to remain in suspension during the carbon dioxide extraction process of the extractor 24. The acidifier 22 also injects acid, such as hydrochloric acid or sulfuric acid, in a concentration in the range from 0.5 to 5 normal into the sewage to provide a pH of approximately 2, and then continuously applies the acidified liquid sewage along line 32 to the extractor 24. The extractor 24 has an elongated chamber, to be described hereinafter, which retains the continuously flowing liquid sewage for a sufficiently long time to permit the completion of a chemical reaction between the acid and inorganic carbonaceous matter, such as calcium carbonate. The reaction has carbon dioxide as one of its products which is ejected along line 34 by means of air which is applied along line 36 to the extractor 24 from the gas supply 28. The mixing of the air on line 36 with the liquid sewage for absorbing the carbon dioxide evolved from the acidification will be described hereinafter with reference to FIG. 5.

After the removal of the carbon dioxide from the inorganic material on line 34, the remaining carbonaceous matter is organic material which is oxidized with an oxidant provided along line 38, the oxidant being air free of carbon dioxide or a mixture of nitrogen and oxygen, to produce carbon dioxide on line 40. The remainder of the liquid of the sewage is discharged as waste along line 42. The operation of the gas supply 28 in supplying the gases on line 36 and 38 to the extractor 24, as well as the supplying of the gases on line 44 for calibrating an analyzer within the system 26 will be described hereinafter with reference to FIG. 3.

As will be seen subsequently with reference to FIG. 5, the gases provided along lines 36 and 38 serve as a transport for carrying the liquid, respectively, through an aeration chamber for the removal of the carbon dioxide from the inorganic matter and through a high temperature reactor for combusting the organic material and the removal of the carbon dioxide evolved therefrom. The use of the gaseous transports is a feature of the invention which inhibits the formation of precipitates and scale within fluid conduits of the extractor 24 and, furthermore, enhances the absorption of carbon dioxide in the aeration chamber and promotes a uniform heating of material in the high temperature reactor to ensure complete combustion of the organic matter.

Referring now to FIG. 2, there is seen a block diagram of the acidifier 22 which receives raw sewage from a tank 46 along line 30, and discharges acidified sewage along line 32 to the extractor 24. In this figure, the line 30 is shown as a tubular conduit for conducting the liquid sewage. The acidifier 22 comprises a cutter 48, a source 50 of a reference sewage of known concentration of carbonaceous matter, a tank 52 for the storage of acid utilized in acidifying the sewage, pumps 54 and 56 for pumping, respectively, sewage and acid, and a selector valve 58 which selects either the raw sewage from the cutter 48 or the reference sewage from the source 50. The cutter 48 may include, by way of example, a motor driven set of blades for breaking up solid matter into relatively small portions and a motor driven grindstone, as disclosed in the aforementioned patent application of G. E. Anderson and G. V. Morris, for further grinding the small portions into fine particulate matter which can remain in suspension in the liquid of the sewage for periods of time up to approximately ½ hour. The outlet of the cutter 48 and the outlet of the reference source 50 are selectively coupled by the selector valve 58 to the pump 54. The tank 52 is coupled via a tubular conduit or line 60 to the pump 56. The outputs of the pumps 54 and 56 are joined via a tubular tee section 62 which combines the sewage pumped by the pump 54 with the acid pumped by the pump 56, the output of the tee 62 appearing on line 32.

Each of the pumps 54 and 56 operates at a predetermined constant speed, the pump 54 pumping the liquid sewage ate a fixed rate of approximately 6 cc (cubic centimeters) per minute while the pump 56 pumps the acid at a fixed rate of approximately 0.05 cc per minute. The selection of the concentration of the acid is based upon the buffering capacity of the sewage in the tank 46 and has a molarity within the aforementioned range of 0.5–5 equivalents per liter. Each of the pumps 54 and 56 is preferably a peristaltic pump wherein rollers are driven along a distensible tube, the rollers progressively squeezing the tube to advance the fluid therein at the predetermined rate.

Referring now to FIG. 3, there is seen a block diagram of the forced gas supply 28 which is seen to comprise tanks 64 and 66 for storing, respectively, air which is free of carbon dioxide and a reference supply of pressurized air containing a predetermined concentration of carbon dioxide. Alternatively, in lieu of the air within the tanks 64 and 66, a pair of tanks (not shown) containing nitrogen and oxygen may be utilized to provide a mixture of 80% and 20% oxygen on line 68 and a mixture of 78% nitrogen, 20% oxygen and 2% carbon dioxide on line 70. While the air provided on line 36 need not be free of carbon dioxide, for convenience, a single tank 64 if shown for supplying both the lines 36 and 38. Two pumps 72 and 74, which may be peristaltic pumps, are coupled via a tee 76 to line 68 for pumping the gas from the tank 64, respectively, along lines 36 and 38 to the extractor 24 of FIG. 1. The pumps 72 and 74 are provided with knobs 78 and 80 which select a predetermined constant speed of pumping. As will be seen, the selectable pumping speed of the pump 74 is particularly useful in calibrating the system 20 of FIG. 1. A line 82 and the line 38 are joined to the pump 74 via a tee 84, the line 82 providing a gas free of carbon dioxide to the analyzer system 26 of FIG. 1. The lines 82 and 70 of FIG. 3 are represented in FIG. 1 by the single line 44. While earlier embodiments of the invention have utilized pure oxygen as the oxidant on line 38, it has been found that a fast moving stream of air free of carbon dioxide or the mixture of 80% nitrogen and 20% oxygen adequately combusts the organic matter of the sewage.

Referring now to FIG. 4, there is seen a block diagram of the system 26 containing an analyzer 86 for the measurement of the concentration of the carbon dioxide applied from the extractor 24 along line 40. A graphical recorder 88 is coupled to the analyzer 86 and provides a record of the carbon dioxide concentration as a function of time. The system 26 also comprises two selector valves 90 and 92 which selectively couple the analyzer 86 to line 40 from the extractor 24 of FIG. 1, or to either the lines 70 and 82 from the gas supply 28 of FIGS. 1 and 3. The analyzer 86 is a standard form of infrared analyzer of carbon dioxide which is available commercially, such as, for example, an infrared analyzer made by the Mine Safety Appliances of Pittsburgh, Pa., having Model No. LIRA300 or LIRA303. Such an infrared analyzer comprises an infrared source and an optical bench including a cell of a reference gas and provides an output electrical signal in response to the interaction of carbon dioxide with the infrared radiation.

The analyzer system 26 is calibrated by setting the selector valves 90 and 92 to admit gas free of carbon dioxide from line 82 in order to obtain a zero reading on the recorder 88, then the selector valve 90 is switched to line 70 to admit the predetermined concentration of carbon dioxide to give a full scale reading on the recorder 88. The entire system 20 of FIG. 1 is then calibrated by setting the selector valve 92 to admit gases from line 40 and the selector valve 58 of FIG. 2 is set to admit sewage from the reference source 50. The pump 74 of FIG. 3 is then adjusted by the knob 80 for adjusting the rate of flow of the oxidant on line 38 until the recorder 88 shows a carbon dioxide concentration consistent with the known concentration of organic carbonaceous material of the reference sewage provided by the source 50 of FIG. 2. This adjustment of calibration permits the system 20 of FIG. 1 to give a continuous reading of the concentration of organic carbonaceous material in the sewage as it continuously flows along line 30 in contradistinction to the batch-type processing utilized by systems of the prior art.

Figure 5:
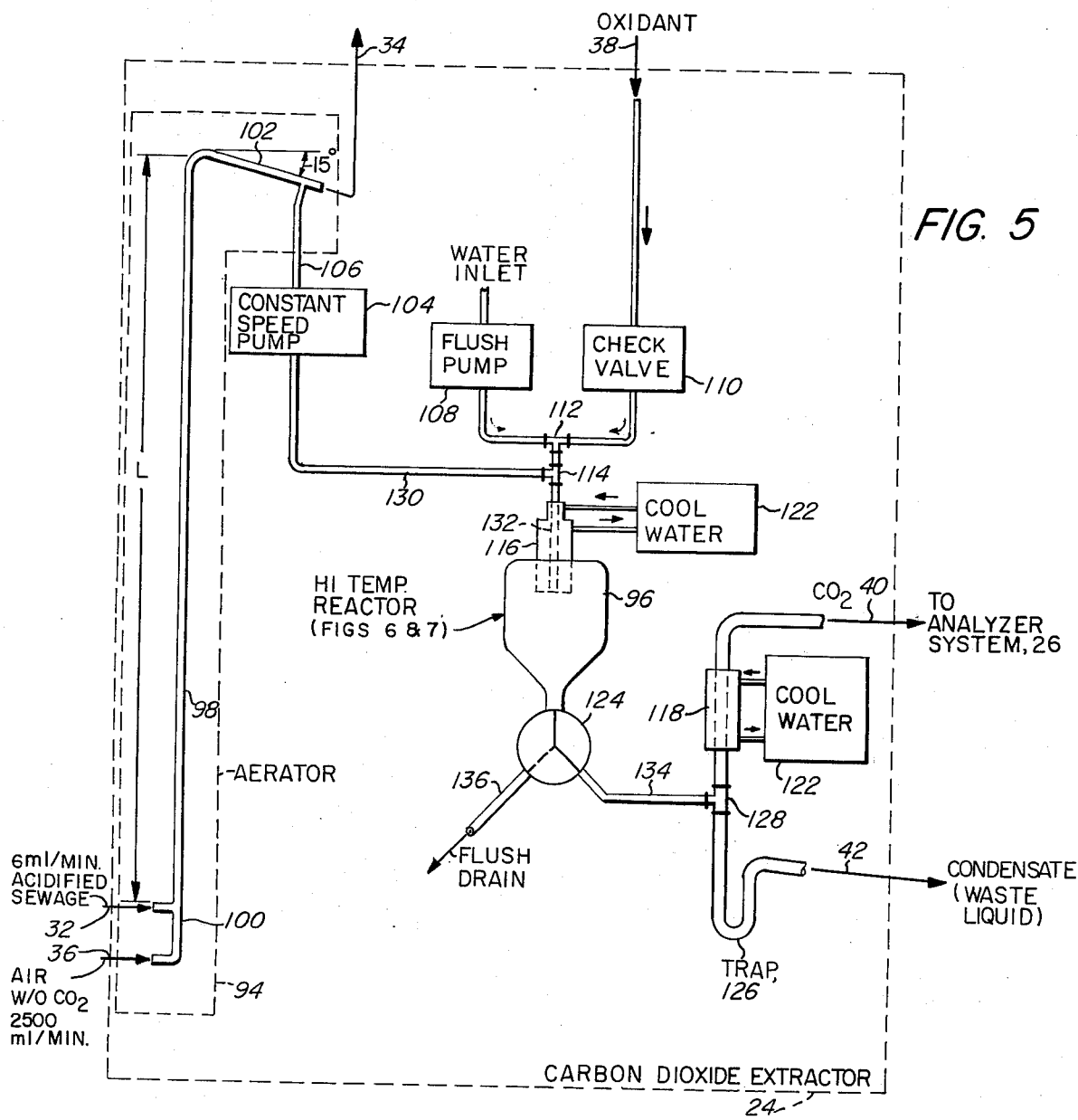
FIG. 5 is a diagram of a carbon dioxide extractor of FIG. 1 disclosing an aeration chamber and combustion chamber of the invention.

Referring now to FIG. 5, there is seen a diagram of the carbon dioxide extractor 24 which comprises an aerator 94 for the removal of carbon dioxide from inorganic matter and a reactor 96 for the removal of carbon dioxide from organic matter. The aerator 94 is composed of a chamber 98 having an elongated tubular form which, in a preferred embodiment of the invention, has a length L of four feet and an inside diameter of approximately ⅛ inch. The aerator 94 is coupled via lines 32 and 36, respectively, to the acidifier 22 and the supply 28 of FIG. 1. The carbon dioxide evolved in the aerator 94 escapes via line 34, seen previously in FIG. 1. Air, free of carbon dioxide, flows into the chamber 98 via line 36 at a rate of approximately 2500 ml/min (milliliters per minute) and joins at a tee 100 with acidified sewage flowing along line 32 at approximately 6 ml/min. Since the volume of the chamber 98 is approximately 10 cc, it is seen that the air flows past the tee 100 at a rate of approximately 16 feet per second, this rate of flow being sufficiently fast to entrain small droplets of the acidified sewage dispersed in a turbulent flow of gas. The chamber 98 is disposed vertically and the viscous forces of the flowing gas are slightly greater than the downward pull of gravity so that the droplets of sewage are seen to rise slowly through the chamber 98. The turbulent environment within the chamber 98 is believed to mitigate against the precipitation of sewage matter upon the walls of the chamber 98 and thereby maintain the aerator 94 free of clogging.

At the top of the aerator 94, a second tee 102 is coupled to the chamber 98 and inclined slightly, at an angle of approximately 15° with the horizontal, with its center leg positioned in a generally downward direction to collect droplets of the sewage while the air with the evolved carbon dioxide escapes through the open sidearm of the tee 102. A pump 104 is coupled to the center leg of the tee 102 via a line 106, the pump 104 being preferably a peristaltic pump, such as the pump 54 of FIG. 2, the pump 104 pumping liquid from the line 106 at a constant rate of approximately 3 ml/min. Since the sewage enters the bottom end of the chamber 98 at the aforementioned rate of 6 ml/min, this being in excess of the fluid flow in the line 106 by an amount of 3 ml/min, the excess liquid also escapes through the open sidearm of the tee 102 at a rate of 3 ml/min in addition to the aforementioned flow of gas at the rate of approximately 2500 ml/min. Thus, it is seen that the line 106 and the center leg of the tee 102 serve as a well for storing sewage from which the carbon dioxide associated with inorganic matter has been removed.

The extractor 24 further comprises a pump 108, a check valve 110, tees 112 and 114, a water jacket 116 which is re-entrant into the reactor 96, a condenser 118, sources 120 and 122 of cool water coupled, respectively, to the water jacket 116 and the condenser 118, a selector valve 124, a trap 126 and a tee 128. The reactor 96, which will be described further with reference to FIGS. 6 and 7, operates at a high temperature in the range of 850° to 1000°C to promote a chemical reaction between organic matter in the sewage delivered by the pump 104 and the oxidizing agent delivered via line 38, seen also in FIG. 1, and the check valve 110. The pump 104 delivers the sewage via line 130 to the center leg of the tee 114. The oxidant, previously disclosed as being either a mixture of air which is free of carbon dioxide or a mixture of nitrogen and oxygen, flows from the check valve 110 via a sidearm and the center leg of the tee 112 into a sidearm of the tee 114 whereupon it joins with the flow of sewage from line 130 and passes via the other sidearm of the tee 114 through the reentrant water jacekt 116 into the reactor 96. Alternatively, pure oxygen may be utilized as the oxidant. Stoichiometrically, approximately 8 ml of oxygen per minute are required for completely combusting the organic matter entering along line 130; however, in the event that pure oxygen is utilized in the preferred embodiment of the invention, approximately 50 times the stoichiometric quantity of oxygen is utilized so that 400 ml/min of oxygen is provided. If the air is utilized, it is applied at the same rate of 400 ml/min even though there is approximately four times as much nitrogen as oxygen, there still being sufficient oxygen for complete combustion. As was noted earlier with reference to FIGS. 3 and 4, the flow rate of the oxidant is set in the calibration of the analyzer system 26. Just as was described previously with reference to the tee 100 in the aerator 94, the high speed gas flow through the tee 114 disperses fine droplets of the sewage liquid entering from line 130 so that the droplets of sewage are thoroughly intermixed with the oxidant as they pass through the water jacket 116. The water jacket 116 maintains the temperature of the sewage therein below boiling temperature so that there is no precipitation of salts or scale at the entry port of the reactor 96; the raising of the temperature of the sewage to the aforementioned high temperature range (850°C–1000°C) and the attendant precipitation of dissolved salts, such as sodium chloride, occurs only within the reactor 96 itself. The sidearms of the tee 114, including the innermost passageway of the water jacket 116, have an inner diameter of one-sixteenth inch in the preferred embodiment of the invention, this inner diameter being one-half the aforementioned inner diameter of the chamber 98, to further increase the speed of the gases rushing past the terminus of the center leg of the tee 114 for increased dispersion of the droplets of sewage in the line 130.

In particular, it is noted that the diameter of the inlet tube 132 to the reactor 96 and the chamber 98 each have inner diameters approximating the diameter of a droplet of water which is believed to promote agitation between liquid and flowing gas directly on the inner surfaces of these tubes to inhibit the formation of precipitates thereon.

In addition to the lack of clogging which is made possible by the aforementioned structure which inhibits the formation of precipitates, a more precise measurement of the carbon dioxide emanating from the organic matter is attained. For example, it has been observed with aerators of sparging systems antedating that of the present invention, that precipitates of organic matter on the interior walls of such sparging systems have a tendancy to flake off at irregular intervals with the result that excessively low values of carbon dioxide are obtained during such time as the organic matter is accumulating on these interior surfaces while excessively large values of carbon dioxide are obtained when the organic precipitates flake off. This is a particularly critical problem in sewage analysis systems employed in situations in which rapid responses in carbon dioxide measurement are required corresponding to rapid changes in the concentration of organic matter in the sewage. The instant system is able to give continuous readings of carbon dioxide which rapidly and accurately follow changes in concentration of organic matter in sewage.

The output of the reactor 96 is coupled by the selector valve 124 to a line 134 and is passed via the line 134 to the condenser 118. The condenser 118 comprises an outer jacket containing the cooling waters from the source 122 for condensing the droplets of liquid sewage and the products of combustion while the carbon dioxide of the combustion proceeds onward via line 40 to the analyzer system 26 of FIG. 1. The condensed liquid flows downwardly through the tee 128 and through the trap 126 to exit via line 42, seen also in FIG. 1, as liquid waste. The liquid within the trap 126 serves the dual functions of inhibiting the escape of carbon dioxide via line 42 as well as preventing the entry of atmospheric carbon dioxide to the analyzer system 26 via the line 42 and the condenser 118.

While the structure of the reactor 96 and the reentrant water jacket 116 substantially inhibits the formation of precipitates and scale within the reactor 96, it has been found that there may be a very gradual accumulation of such scale which is preferably removed at intervals of approximately once per week. This removal of scale is accomplished by energizing the flush pump 108 to force water through the tees 112 and 114 and through the inlet tube 132 to pass through the reactor 96 for dissolving out soluble salts, such as the aforementioned sodium chloride, the cold water serving to dislodge such scale by the suddenly induced dimensional changes due to the sudden change in temperature of the reactor 96 from a typical operating temperature, such as the aforementioned 1000°C to the temperature of cool water. During the flushing operation, the selector valve 124 is coupled in its alternate position to a drain tube 136 so that the flushing water passes through the drain tube 136 rather than through the line 134. During the flushing operation, the check valve 110 prevents the flush water from entering the oxidant line 38. It is also noted that, by way of alternative embodiment to be disclosed with reference to FIGS. 8–10, a condenser similar to the condenser 118 may be mounted directly beneath the reactor 96 to ensure that the reactor effluent has been cooled prior to its reaching the selector valve 124. In that embodiment, the flushing water would pass through the condenser and the selector valve 124 would ensure that the flush water would not pass via line 40 to the analyzer system 26.

Figure 6:
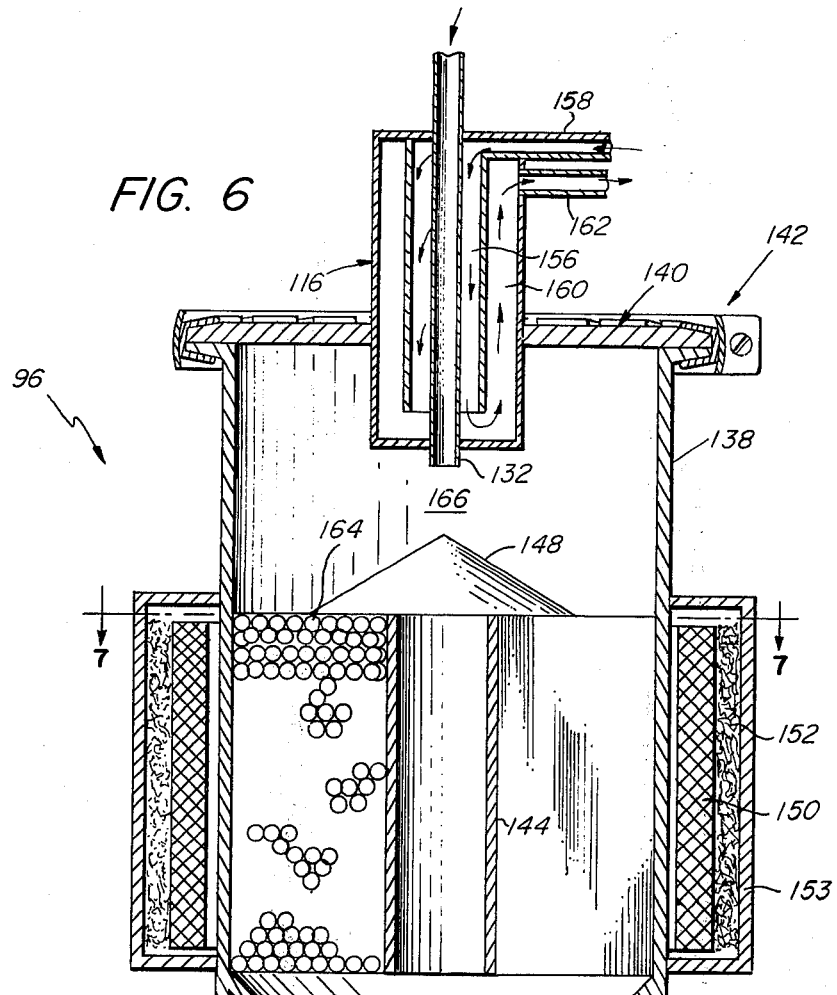
FIG. 6 is an axial sectional view of the combustion chamber.
Figure 7:
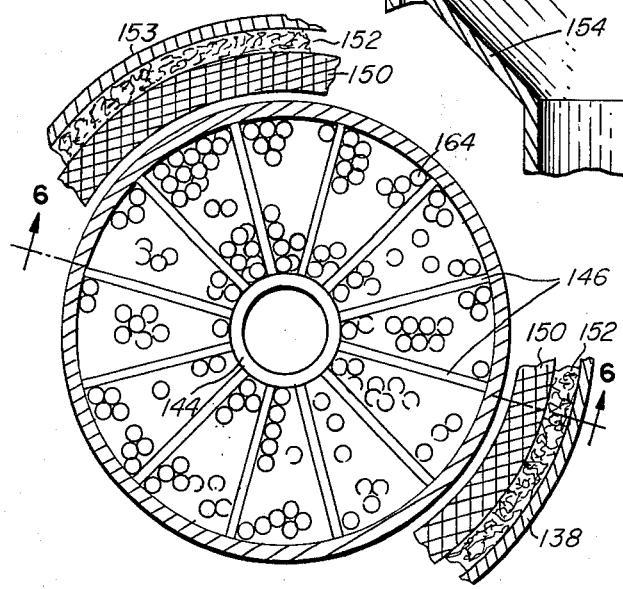
FIG. 7 is a sectional view of the combustion chamber taken along the line 7—7 in FIG. 6.

Referring now to FIGS. 6 and 7, there are shown, respectively, a longitudinal sectional view of the reactor 96 taken along the line 6—6 of FIG. 7, and a sectional view of the reactor 96 taken transversely of the longitudinal axis along the line 7—7 of FIG. 6. The reactor 96 comprises an outer pipe 138, a cover 140 affixed via a V-band retainer ring assembly 142 to the upper rim of the outer pipe 138 and having a central aperture through which the water jacket 116 passes and is secured to the cover 140, an inner pipe 144 which is joined to the outer pipe 138 by vanes 146, the pipes 138 and 144 and the vanes 146 being fabricated from a material such as inconel metal which is substantially inert to the sewage material even at the elevated temperatures of approximately 1000°C, a conically-shaped cover to be referred to hereinafter as a hat 148 positioned beneath the inlet tube 132 and secured to the inner pipe 144 for directing the flow of effluent from the inlet tube 132 to the region between the inner pipe 144 and the outer pipe 138, heater elements 150 enclosed along their exterior by thermal insulation 152 and positioned by a casing 153 around the exterior of the outer pipe 138, and a funnel-shaped base 154 secured to the bottom of the outer pipe 138.

The water jacket 116 is seen to comprise an inner chamber 156 coupled to an inlet tube 158, and an outer chamber 160 joined at its lower end to the inner chamber 156 and at its upper end to an outlet tube 162, seen also in FIG. 5. Cool water from the aforementioned source 120 passes downwardly through the inner chamber 156 and upwardly through the outer chamber 160 for cooling the inlet tube 132 by removing heat conducted thereto by radiation from the heater elements 150 and by conduction through the cover 140.

In a preferred embodiment of the invention, alumina balls 164 are placed in the regions between the vanes 146 for providing a tortuous path with the attendant improved dispersion of and heating of matter entering the reactor 96 via the inlet tube 132. The inner pipe 144 has an outer diameter of approximately 1.6 inches and a length of approximately seven inches. The inner diameter of the outer pipe 138 is approximately three inches.

In operation, therefor, the heater elements 150, which are energized by an external source of electric power (not shown), supply 1600 watts of heat to the reactor 96, the heat being communicated via the outer pipe 138, the cover 140, the vanes 146 and the hat 148 to an antechamber 166 having an axial length of approximately four inches which preheats the effluent of the inlet tube 132 as the effluent travels from the bottom end of the inlet tube 132 to the hat 148. The heat is further communicated via the vanes 146 to the inner pipe 144 and to the balls 164 for vaporizing any water admitted via the inlet tube 132 and for combusting organic matter with oxygen admitted via the inlet tube 132. The volume of the reactor 96 and the length of the tortuous paths between the balls 164 in combination with the aforementioned rates of gaseous and liquid sewage flow through the inlet tube 132 provide for sufficient retention time within the reactor 96 to ensure complete combustion of the organic sewage matter with the oxygen. The balls 164 are fabricated from the aforesaid alumina since the alumina has been found to communicate heat to the gases passing through the reactor 96 while being substantially inert to chemical reactions with the organic matter of the sewage and with the oxygen and nitrogen admitted by the inlet tube 132. The base 154 may be made of copper, if desired, to further ensure complete combustion since copper acts as a catalyst for the combustion.

Figure 9:
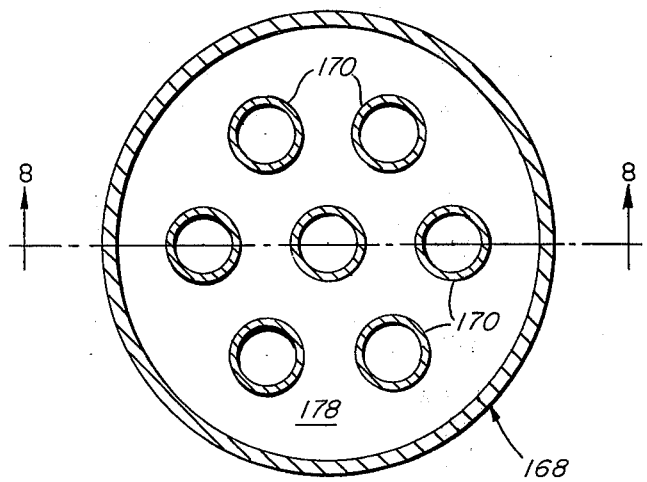
FIG. 9 is a sectional view of the condenser taken along the line 9—9 of FIG. 8.

Referring now to FIGS. 8 and 9, there are shown views of a condenser 168, FIG. 8 showing a sectional view taken along a longitudinal axis of the condenser 168 along line 8—8 of FIG. 9, and FIG. 9 showing a sectional view taken transversely of the longitudinal axis along line 9—9 of FIG. 8. The condenser 168 is utilized in an alternative embodiment of the system 20 of FIG. 1 and replaces the condenser 118 of FIG. 5, the condenser 168 being secured to the outlet at the bottom of the base 154 of the reactor 96 and serving to couple the reactor 96 to the selector valve 124 of FIG. 5. The condenser 168 comprises a set of seven tubes 170 which are spaced apart to permit the flow of cooling water among them and which are coupled between an inlet chamber 172 and an outlet chamber 174. The inlet chamber 172 has a curved floor member 176 having apertures therein for positioning the upper ends of each of the tubes 170. The outlet chamber 174 has a floor member 178 having apertures for the positioning of the lower ends of the tubes 170. The condenser 168 is enclosed by an outer case 180 having an upper end section 182, which is an extension of the outer pipe 138 of FIG. 6, and a lower end section 184 to which are secured, respectively, the floor members 176 and 178. The upper end section 182 accepts the base 154 of the reactor 96 while the lower end section 184 is flared to form an exit port 185. An inlet tube 186 positioned near the lower end section 184 admits water to the water chamber 188 which comprises the region bounded between the curved floor members 176 and 178 and the space between the tubes 170. An outlet tube 190 positioned nearer the upper end section 182 allows the exit of cooling water from the water chamber 188. The exit port 185 is coupled to the trap 126 via the selector valve 124.

Figure 10:
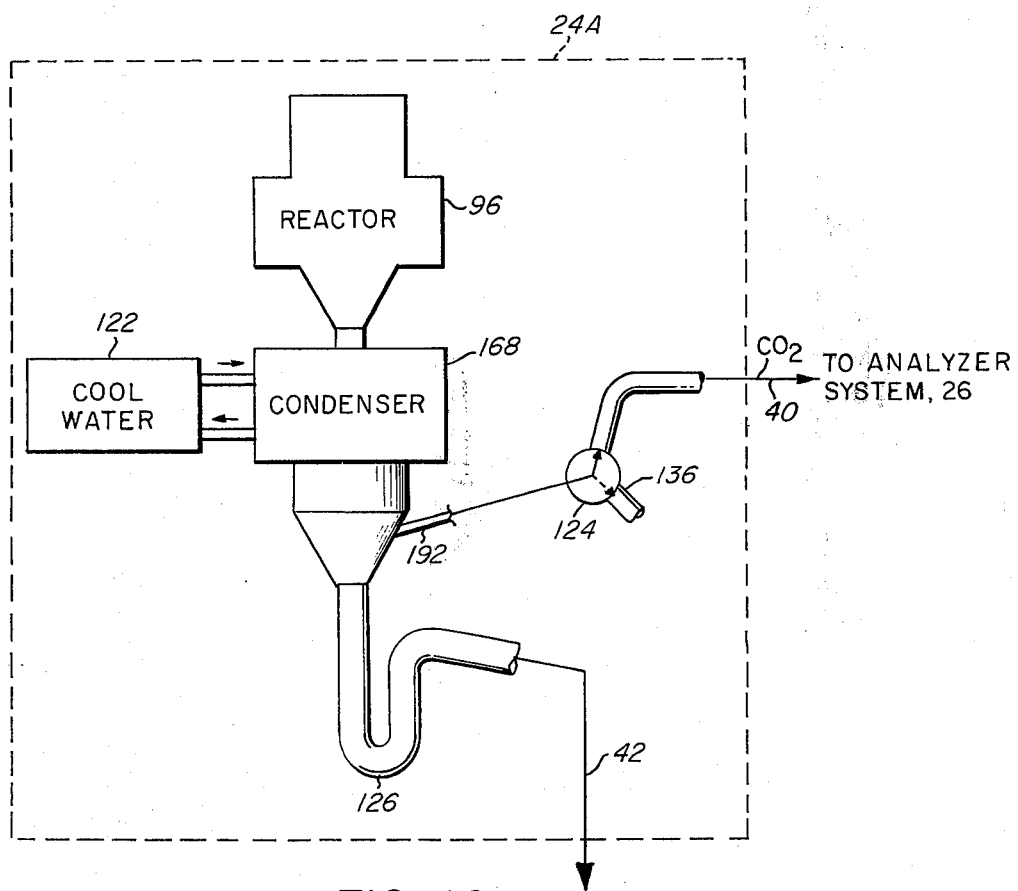
FIG. 10 shows diagrammatically the interconnection of the condenser of FIGS. 8 and 9 with components of the extractor of FIG. 5.

Referring also to FIG. 10, there is seen a diagram of a portion of the extractor 24 in the alternative embodiment wherein the condenser 168 is coupled to the base of the reactor 96. A tube 192 angled in a downward direction within the outlet chamber 174 couples gases therefrom to the analyzer system 26 via the selector valve 124. The lower end section 184 is seen coupled to the trap 126 whereby condensed gases, particularly water, exit from the outlet chamber 174 to escape as waste liquid on line 42. In this alternative embodiment of the reactor 24A, the coupling of the trap 126 and the selector valve 124 are seen to have a different arrangement from that utilized with the extractor 24 of FIG. 5.

In operation, therefor, the condenser 168 conducts exhaust gases from the reactor 96 through the tubes 170 which are surrounded by the cooling water of the water chamber 188, the cooling water also chilling the curved floor 176 of the inlet chamber 172, so that all of the substances exiting from the base 154 of the reactor 96 experience a sudden chilling. It has been observed, experimentally, that this rapid chilling inhibits the adherence of precipitating material upon the inner walls of the condenser 168 which come in contact with the effluent of the reactor 96 as well as the inner surface of the tube 192 through which the exhaust gases are conducted to the analyzer system 26. In the event that, over a long period of usage, a scale of adhering precipitous matter is formed along the aforesaid inner surfaces of the condenser 168, there is provided an array of jets 192 and an array of jets 194 connected via lines 196 to a source 198 of high pressure water and which are positioned for directing streams of water, respectively, against the lower tip of the base 154 and against the curved floor 176 and into the tubes 170 for flushing away such adhering scale. The flushing waters promote sudden cooling with attendant dislodging of scale and are passed via the exit port 185 in the lower end section 184 to be discharged via the trap 126. The aforementioned flushing of the reactor 96 via the flush pump 108 of FIG. 5 may also be employed in this embodiment of the invention in which case the flushing waters pass through both the reactor 96 and the condenser 168 to exit via the trap 126. During these flushing operations, the selector valve 124 of FIG. 10 is advantageously switched to couple the tube 192 to the drain tube 136 so that any flushing waters which enter the tube 192 can be discharged via the drain tube 136 to prevent their passing on to the analyzer system 26.

It is understood that the above-described embodiments of the invention are illustrative only and that modifications thereof may occur to those skilled in the art. Accordingly, it is desired that this invnetion is not to be limited to the embodiments disclosed herein but is to be limited only as defined by the appended claims.

What is claimed is:

1. An organic carbon analyzer system for analyzing material such as that found in raw sewage containing inorganic and organic carbonaceous substances, said system comprising:
   means for treating said material with a chemical reagent that reacts with inorganic carbonaceous substances to produce a volatile compound of carbon;
   means coupled to said treating means for dispersing said material in a first gaseous carrier, said first gaseous carrier being an absorber of said volatile compound, said dispersing means comprising an elongated chamber and means located at one end thereof for forcing a gas past a source of said material to urge said material to flow in a common current with said gas and thereby serve as said gaseous carrier for said material and inhibit the formation of a scum along the interior surface of said tube, said source of said material being located adjacent said one end of said elongated chamber;

means coupled to said dispersing means for replacing said first gaseous carrier with a second gaseous carrier free of said volatile compound, said second gaseous carrier reacting with organic carbonaceous substances to produce said volatile compound of carbon; and means coupled to said replacing means for measuring the concentration of said volatile compound in said second gaseous carrier, the amount of said concentration being a measure of the amount of organic carbonaceous substances in said material.

2. A system according to claim 1 wherein said treating means is adapted to receive a continuous flow of said material.

3. A system according to claim 2 wherein said treating means comprises means for injecting an acid into said continuously flowing material, and wherein said volatile compound is carbon dioxide.

4. An organic carbon analyzer system for analyzing material such as that found in raw sewage containing inorganic and organic carbonaceous substances, said system comprising:

means for treating said material with a chemical reagent that reacts with inorganic carbonaceous substances to produce a volatile compound of carbon;

means coupled to said treating means for dispersing said material in a first gaseous carrier, said first gaseous carrier being an absorber of said volatile compound, said dispersing means comprising a vertically oriented tube and means located at a lower end thereof for forcing a gas upwardly past a source of said material to entrap portions of said material with a viscous drag in a common current with said gas to raise said material against the force of gravity and thereby serve as said gaseous carrier for said material, said source of said material being located adjacent said lower end of said tube, said gas being guided within said tube and having a sufficient speed for inducing a turbulent flow of said gas which inhibits the formation of a scum along the interior surface of said tube;

means coupled to said dispersing means for replacing said first gaseous carrier with a second gaseous carrier free of said volatile compound, said second gaseous carrier reacting with organic carbonaceous substances to produce said volatile compound of carbon, and wherein said material is a suspension of sewage matter in a liquid, and wherein said dispersing means includes means for inserting said material into said moving gas; and means coupled to said replacing means for measuring the concentration of said volatile compound in said second gaseous carrier, the amount of said concentration being a measure of the amount of organic carbonaceous substances in said material.

5. A system according to claim 1 wherein said measuring means includes means for separating said volatile compound from said second gaseous carrier and said material, said separating means including a condenser for cooling said second gaseous carrier and said volatile compound and said material, said separating means permitting said material to fall away from said volatile compound and said second gaseous carrier.

6. A system according to claim 1 wherein said replacing means comprises means for separating said material from said first gaseous carrier and said absorbed volatile compound.

7. A system according to claim 6 wherein said material is a suspension of sewage matter in a liquid, and wherein said replacing means comprises a tube of moving gas and means for inserting said liquid into said moving gas, said moving gas serving as said second gaseous carrier.

8. An organic carbon analyzer system for analyzing material such as that found in raw sewage containing inorganic and organic carbonaceous substances, said system comprising:

means for treating said material with a chemical reagent that reacts with inorganic carbonaceous substances to produce a volatile compound of carbon;

means coupled to said treating means for dispersing said material in a first gaseous carrier, said first gaseous carrier being an absorber of said volatile compound, said dispersing means comprising means for forcing a gas upwardly past a source of said material to entrap portions of said material with a viscous drag to raise said material against the force of gravity and thereby serve as said gaseous carrir for said material, said gas being guided within a vertically oriented tube and having a sufficient speed for inducing a turbulent flow of said gas which inhibits the formation of a scum along the interior surface of said tube, and wherein said material is a suspension of sewage matter in a liquid, and wherein said dispersing means includes means for inserting said material into said moving gas;

means coupled to said dispersing means for replacing said first gaseous carrier with a second gaseous carrier free of said volatile compound, said second gaseous carrier reacting with organic carbonaceous substances to produce said volatile compound of carbon, and wherein said replacing means includes means coupled to said tube at a point of entry of said material into said tube for separating said material from said gaseous carrier; and means coupled to said replacing means for measuring the concentration of said volatile compound in said second gaseous carrier, the amount of said concentration being a measure of the amount of organic carbonaceous substances in said material.

9. A system according to claim 8 wherein said replacing means is formed of a tee section of tubing inclined downwardly towards an exit point of gas therefrom and having a downwardly projecting center leg for the entrapment of drops of said liquid.

10. An organic carbon analyzer system for analyzing material such as that found in raw sewage containing inorganic and organic carbonaceous substances, said system comprising:

means for treating said material with a chemical reagent that reacts with inorganic carbonaceous substances to produce a volatile compound of carbon;

means coupled to said treating means for dispersing said material in a first gaseous carrier, said first gaseous carrier being an absorber of said volatile compound, said dispersing means comprising means for forcing a gas upwardly past a source of said material to entrap portions of said material with a viscous drag to raise said material against the force of gravity that thereby serve as said gaseous carrier for said material, said gas being guided within a vertically oriented tube and having a sufficient speed for inducing a turbulent flow of said gas which inhibits the formation of a scum along the interior surface of said tube;

means coupled to said dispersing means for replacing said first gaseous carrier with a second gaseous carrier free of said volatile compound, said second gaseous carrier reacting with organic carbonaceous substances to produce said volatile compound of carbon, and wherein said replacing means comprises means for separating said material from said first gaseous carrier and said absorbed volatile compound, said material being a suspension of sewage matter in a liquid, and said replacing means comprising a tube of moving gas and means for inserting said liquid into said moving gas, said moving gas serving as said second gaseous carrier; and wherein said inserting means has the form of a tee section in said tube, said moving gas moving with sufficient speed relative to a speed of movement of said liquid for dispersing said liquid within said gas such that said gas carries said liquid away from said tee section drop by drop; and means coupled to said replacing means for measuring the concentration of said volatile compound in said second gaseous carrier, the amount of said concentration being a measure of the amount of organic carbonaceous substances in said material.

11. A system according to claim 10 wherein said replacing means further comprises a chamber coupled to said tube, said liquid of said tube being downwardly transported by said gaseous carrier into said chamber, said chamber having means coupled thereto for elevating the temperature thereof to induce said reacting of said material with said second gaseous carrier to provide said volatile compound, said chamber having means positioned within said chamber and facing said tube for directing said liquid and said second gaseous carrier to a portion of said chamber adjacent said temperature elevating means.

12. A system according to claim 11 wherein said volatile compound is carbon dioxide.

13. A system according to claim 12 wherein said directing means has a conical shape with its axis positioned along a center line of the chamber.

14. In combination:

means for forcing a gas upwardly past a source of liquid sewage capable of suspending solid particles within said sewage, said gas entrapping droplets of said liquid with a viscous drag comparable to the force of gravity acting on droplets of said liquid;

means for separating said gas from said entrapped droplets of liquid;

means for dispersing said separated droplets of liquid into a second stream of gas;

means for heating said second stream of gas and said droplets of liquid dispersed therein, said heating means being configured to direct said second stream of gas towards a region thereof having a maximum temperature for allowing a chemical reaction induced by said heating to go substantially to completion between material suspended within said liquid sewage and said second gas; and means coupled to said heating means for condensing said second gas and products of said chemical reaction to separate out solid mattter remaining after said chemical reaction.

15. A combination according to claim 14 further comprising means coupled to said condensing means for measuring the concentration of gaseous products of said chemical reaction contained within said second gas.

16. A combination according to claim 15 further comprising means for flushing said heating means with cold water to dissolve encrusted salts resulting from said heating of said flowing gases.

17. A combination according to claim 15 further comprising means for flushing said condensing means with cold water to wash away solid precipitates of material remaining after said chemical reaction, said condensing means having an interior chamber coupled to a heated portion of said heating means and passageways extending downstream of said interior chamber which are cooled by cold water of said condensing means, said condensing means having jets positioned within said interior chamber for directing said flushing water along interior walls of said interior chamber and into said passageways.

18. In combination:

means for directing a gas upwardly past a source of liquid capable of suspending solid particles therein, said gas entrapping droplets of said liquid with a viscous drag comparable to the force of gravity acting on droplets of said liquid;

means coupled to said directing means for separating said gas from said entrapped droplets of liquid;

means coupled to said separating means for dispersing said separated droplets of liquid into a second stream of gas which reacts with material within said liquid to produce a gaseous product; and means coupled to said dispersing means for measuring the concentration of said gaseous product.

* * * * *

UNITED STATES PATENT OFFICE
CERTIFICATE OF CORRECTION

Patent No. 3,964,868    Dated June 22, 1976

Inventor(s) Louis S. DiCola, Donald W. Kemp, Duane Evans

It is certified that error appears in the above-identified patent and that said Letters Patent are hereby corrected as shown below:

Column 4, line 36, change "ate" to -- at --

Column 4, line 55, after "80%" insert -- nitrogen --

Column 6, line 53, change "jacekt" to -- jacket --

Column 7, line 34, change "of" to -- or --

Column 10, line 50, change "invnetion" to -- invention --

Column 10, line 66, after "thereof" leave a space

Column 12, line 26, change "carrir" to -- carrier --

Column 12, line 40, after "point" insert -- above a point --

Signed and Sealed this

Twenty-third Day of November 1976

[SEAL]

Attest:

RUTH C. MASON
Attesting Officer

C. MARSHALL DANN
Commissioner of Patents and Trademarks